United States Patent
Mandge et al.

(10) Patent No.: US 11,931,370 B2
(45) Date of Patent: Mar. 19, 2024

(54) STABLE PHARMACEUTICAL COMPOSITIONS OF CYCLOPHOSPHAMIDE

(71) Applicant: Slayback Pharma LLC, Princeton, NJ (US)

(72) Inventors: Shailendra Mandge, Hyderabad (IN); Harish Gunda, Nizamabad (IN); Naga Venkata Durga Prasad Ketha, Hyderabad (IN); Venkateshwar Reddy Keesara, Hyderabad (IN); Satheesh Balasubramanian, Hyderabad (IN); Sumitra Ashokkumar Pillai, Hyderabad (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 17/961,943

(22) Filed: Oct. 7, 2022

(65) Prior Publication Data
US 2023/0119069 A1     Apr. 20, 2023

(51) Int. Cl.
| | | |
|---|---|---|
| *A01N 43/00* | (2006.01) | |
| *A01N 43/46* | (2006.01) | |
| *A61K 9/00* | (2006.01) | |
| *A61K 9/08* | (2006.01) | |
| *A61K 31/55* | (2006.01) | |
| *A61K 31/675* | (2006.01) | |
| *A61K 47/10* | (2017.01) | |
| *A61K 47/14* | (2017.01) | |

(52) U.S. Cl.
CPC .......... *A61K 31/675* (2013.01); *A61K 9/0053* (2013.01); *A61K 9/08* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 4,879,286 A * | 11/1989 | Alam | A61K 31/675 514/110 |
| 9,662,342 B2 | 5/2017 | Palepu et al. | |
| 10,849,916 B2 | 12/2020 | Shaik et al. | |
| 10,993,952 B2 | 5/2021 | Chandrashekhar et al. | |
| 2014/0005148 A1 | 1/2014 | Neelakantan et al. | |
| 2017/0143744 A1* | 5/2017 | Shaik | A61K 9/0019 |
| 2019/0350948 A1* | 11/2019 | Shaik | A61K 9/19 |
| 2020/0069678 A1 | 3/2020 | Mehta et al. | |
| 2022/0265688 A1 | 8/2022 | Naidu et al. | |

FOREIGN PATENT DOCUMENTS

| | | | | |
|---|---|---|---|---|
| CA | 3059674 A1 * | 10/2018 | | A61K 31/506 |
| CN | 111643488 A | 9/2020 | | |
| WO | 2020/178725 A1 | 9/2020 | | |
| WO | 2022/038072 A1 | 2/2022 | | |

OTHER PUBLICATIONS

International Search Report and Written Opinion of the International Searching Authority for International Application No. PCT/US2022/046058, dated Jan. 30, 2023.

* cited by examiner

*Primary Examiner* — Layla Soroush
(74) *Attorney, Agent, or Firm* — Birch, Stewart, Kolasch & Birch, LLP

(57) ABSTRACT

The present invention relates to stable liquid oral compositions of cyclophosphamide having extended stability, methods for their administration, processes for their production, and use of these compositions for treatment of diseases treatable by cyclophosphamide. The invention also relates to a kit comprising stable liquid oral compositions of cyclophosphamide.

4 Claims, 1 Drawing Sheet

| Part-1 (Oily Component) | Part-2 (Alcohol Component) |
|---|---|
| Melt Cremophor® RH 40 at 45°C until clear solution forms. | Kept for slow stirring |
| Cremophor® ELP is added to above step and kept for stirring until clear solution forms. Maintain the temperature at 35°C. | Tartaric acid is added to the above step with continued stirring |
| Oleic Acid is added to the above step with stirring till clear solution forms. Maintain the temperature at 35°C. | Propyl Gallate is added to the above step with continued stirring |
| Maisine® CC is added to the above step with stirring till clear solution forms. Maintain the temperature at 35°C. | Sucralose is added to the above step with continued stirring |
| Phosal® 50 PG is added to the above step and kept for stirring until clear solution forms. Maintain the temperature at 35°C. | L-menthol is added to the above step with continued stirring |
| Cyclophosphamide Monohydrate is added to the above step with stirring until clear solution forms | Mixed Berry Flavor, Banana Flavor, Magna sweet 110 and were added to the above step with stirring |
| 50% of Batch Qty Labrafac® Lipophile WL1349 is added to above step and kept for stirring until clear solution forms. After complete dissolution, stop heating and to room temperature. | |
| Slowly add part 2 mixture to part 1 mixture with slow stirring until clear solution forms. Rinse the part-2 container 2 times with Labrafac® Lipophile WL1349 and mix in above mixture | |
| Makeup final volume with Labrafac® Lipophile WL1349 | |

STABLE PHARMACEUTICAL COMPOSITIONS OF CYCLOPHOSPHAMIDE

CROSS-REFERENCE TO RELATED APPLICATIONS

This application claims foreign priority to Indian Application No. IN 202141046000, filed on Oct. 8, 2021, which is incorporated herein by reference in its entirety.

FIELD OF THE INVENTION

The present disclosure relates to stable liquid oral compositions of cyclophosphamide having extended stability, methods for their administration, processes for their production, and use of these compositions for treatment of diseases treatable by cyclophosphamide. The invention also relates to a kit comprising stable liquid oral compositions of cyclophosphamide.

BACKGROUND OF THE INVENTION

Cyclophosphamide is a widely used cytotoxic nitrogen mustard that exerts anti-neoplastic effects through alkylation and cross-linking of DNA. Cyclophosphamide is a prodrug that undergoes enzymatic and chemical activation to its active metabolites in liver. The cyclophosphamide active metabolites are responsible for slowing the growth of cancer cells; and they eventually get eliminated through kidneys.

Chemically, cyclophosphamide is related to a group of novel cyclic phosphoric acid ester amides. The chemical name of cyclophosphamide monohydrate is 2-[bis(2-chloroethyl)amino]tetrahydro-2H-1,3,2-oxaza phosphorine-2-oxide monohydrate and its chemical structure is represented by structural formula (I):

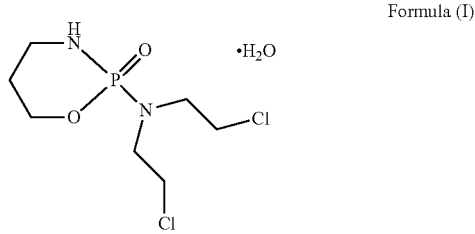 [SMILES: O=P1(N(CCCl)CCCl)NCCCO1 ; O]

Formula (I)

Cyclophosphamide is currently approved and marketed in US as tablets, capsules, and injectable dosage forms for treatment of malignant diseases in adult and pediatric patients. It is also indicated for treatment of biopsy proven minimal change nephrotic syndrome (MCNS) in pediatric patients who have failed to adequately respond to, or are unable to tolerate adrenocorticosteroid therapy. MCNS is one of the three distinct histological variants of idiopathic nephrotic syndrome. Idiopathic nephrotic syndrome has a reported incidence of two to seven cases per 100,000 children and a prevalence of nearly 16 cases per 100,000. Age, at initial presentation has a great impact on the disease distribution frequency. 70% of MCNS patients are younger than 5 years; 20-30% of adolescent nephrotic patients have MCNS. The recommended oral dose of cyclophosphamide for treatment of MCNS is based on patient body weight i.e., 2 mg per kg daily for 8 to 12 weeks (maximum cumulative dose of 168 mg per kg).

Cyclophosphamide is used for the treatment of malignant diseases such as Hodgkin's disease, lymphocytic lymphoma, mixed-cell type lymphoma, histiocytic lymphoma, Burkitt's lymphoma, multiple myeloma, chronic lymphocytic leukemia, chronic granulocytic leukemia, acute myelogenous and monocytic leukemia, acute lymphoblastic leukemia, mycosis fungoides, neuroblastoma, adenocarcinoma of the ovary, retinoblastoma, and carcinoma of the breast.

The recommended oral cyclophosphamide dosing for adults and pediatric patients is in the range of 1 mg per kg per day to 5 mg per kg per day for both initial and maintenance dosing. Specific cyclophosphamide dosing must be adjusted based on anti-tumor activity, total leukocyte count and renal function. In other words, the dose of cyclophosphamide administered to individual patients may vary depending on the specific indication, severity of the clinical condition, body weight of the patient, anti-tumor activity, total leukocyte count and renal function of the patient.

Cyclophosphamide has a relatively narrow therapeutic index, i.e., narrow window between their effective dose and toxic dose. Because of the narrow therapeutic index, small changes in the dosage of cyclophosphamide can potentially lead to sub-therapeutic or toxic effects. Toxic effects include cardiotoxicity, nephrotoxicity, neurotoxicity, infertility, bladder toxicity, myelosuppression and leukemogenesis.

Individual dose requirements of patients and relatively narrow therapeutic index of cyclophosphamide necessitates a suitable dosage form which is sufficiently flexible to allow accurate dosing and enables optimal dose adjustments based on individual patient needs.

In order to cater to the needs of individual adult and pediatric patient populations, health care professionals and caregivers manipulate the available solid and injectable dosage forms of cyclophosphamide by a process referred to as compounding. One approach during compounding is to extemporaneously prepare an oral liquid from Cytoxan® (cyclophosphamide powder for injection), wherein the powder for injection is first reconstituted with 0.9% normal saline, and the final volume made up with vehicles such as Ora-plus® or simple syrup. Such manipulated oral dosage forms have a very short shelf life at room temperature.

Manipulated dosage forms prepared by compounding fall outside the regulatory agency approval process and are associated with safety and efficacy concerns. Lack of appropriate drug formulations for children can lead to increased risk of errors and adverse events, lack of adherence because of taste issues, and sub-optimal dosing leading to therapeutic failure. Compounding practice uses time, money, and resources that could be directed to other aspects of pharmacy-related patient care if commercially available formulations were available.

Handling of cyclophosphamide during compounding presents safety concerns. Cyclophosphamide is a cytotoxic drug. Hospital personnel i.e., pharmacy technicians, oncology nurses, and caregivers need to exercise caution when compounding cyclophosphamide oral doses. To minimize the risk of dermal exposure, health care personnel are advised to wear gloves when handling vials containing cyclophosphamide for Injection, USP. Several studies have shown that exposure to cyclophosphamide can cause reproductive toxic effects as well as carcinogenic effects. The hospital personnel or caregivers could be dermally exposed to cyclophosphamide while performing their daily duties. Exposure occurs predominantly through hands and sporadically through other body locations such as forehead and forearms. Thus, it is important to minimize or avoid cyclophosphamide topical exposure while administering the drug to the patient.

Storage and stability of manipulated dosage forms are additional concerns. Aqueous cyclophosphamide suspensions or solutions have a very short shelf life at room temperature, and such preparations should be stored under refrigerated condition and used within 14 days.

Shorter shelf life of aqueous liquid compositions of cyclophosphamide is attributed to the unique physical and chemical properties of cyclophosphamide, particularly to its nature to undergo rapid hydrolytic degradation. Cyclophosphamide undergoes rapid hydrolysis in aqueous environment. Rate of hydrolysis depends on pH of solution and the temperature at which solution or suspension is being stored. Cyclophosphamide decomposes at a considerably higher rate when the temperature is elevated. However, because of the need for immediate availability and frequent dosing requirement, cyclophosphamide liquid preparations are often compounded in small quantities and stored under refrigeration in glass containers and used within 14 days.

Rapid hydrolytic degradation of cyclophosphamide at room temperature in aqueous environment presents a challenge in formulating cyclophosphamide liquid oral compositions. As per drug product recommendations, all commercially available liquid injectable dosage forms of cyclophosphamide are stored at 2 to 8° C. to retard loss of potency and their diluted solutions are used within 24 hours when stored at room temperature. Partially used undiluted solutions are used within 28 days when stored at 2-8° C. after their first use. Because of these recommended storage conditions, there is a significant amount of cyclophosphamide dose wastage which hinders using multi-dose units of cyclophosphamide for prolonged duration of time after their first use.

It is evident that liquid preparations of cyclophosphamide are not stable for more than 24 hours when stored at room temperature. It is very challenging to manufacture oral liquid compositions of cyclophosphamide which are stable at room temperature for more than 14 days.

Thus, there is a need to develop cyclophosphamide compositions suitable for oral administration that remain stable over extended periods of time under suitable storage conditions. There also exists a need for developing novel compositions of cyclophosphamide that are safe-to-administer, and which minimizes or prevents degradation of cyclophosphamide.

As noted above, preparing stable liquid compositions of cyclophosphamide is quite challenging due to the inherent rapid hydrolytic degradation exhibited by cyclophosphamide. Attempts have been previously made in order to formulate stable oral liquid compositions of cyclophosphamide. However, successful development of stable oral liquid compositions of cyclophosphamide has remained a challenge particularly because of the poor stability exhibited by cyclophosphamide in aqueous environment.

Because of the problems associated with commercially approved products and manipulated dosage forms of cyclophosphamide, it is desirable to develop novel stable liquid compositions of cyclophosphamide suitable for oral administration to human subjects, which are safe-to-administer, which allow flexibility in administration of doses to adult and pediatric population, which are therapeutically effective, and exhibit prolonged room temperature stability without any significant loss of potency enabling optimal usage of cyclophosphamide compositions.

The present invention fulfils this need by developing stable oral liquid compositions of cyclophosphamide to achieve an improved standard of patient care.

SUMMARY OF THE INVENTION

In an aspect, the present invention relates to a stable pharmaceutical composition for oral administration comprising (i) cyclophosphamide, and (ii) non-aqueous solvent; wherein the composition is stable at room temperature.

In an aspect, the present invention relates to a stable pharmaceutical composition for oral administration comprising (i) cyclophosphamide, and (ii) non-aqueous solvent; wherein the composition is stable at room temperature for at least 1 month.

In an aspect, the present invention relates to a stable pharmaceutical composition for oral administration comprising (i) cyclophosphamide, and (ii) non-aqueous solvent; wherein the composition is stable at 25° C./60% RH for at least 3 months.

Another aspect of the present invention relates to a stable pharmaceutical composition for oral administration comprising (i) cyclophosphamide, (ii) non-aqueous solvent, and (iii) co-solvent; wherein the composition is stable at 25° C./60% RH for at least 3 months.

In certain aspects of the invention as described above, the non-aqueous solvent is a lipid solvent, wherein the lipid solvent is selected from a group consisting of medium-chain fatty acids, medium-chain fatty acid esters of glycerol, medium-chain fatty acid esters of polyethylene glycol, medium-chain fatty acid esters of propylene glycol, long-chain fatty acids, long-chain fatty acid esters of glycerol, long-chain fatty acid esters of polyethylene glycol, or long-chain fatty acid esters of propylene glycol.

In certain aspects of the invention as described above, the co-solvent is selected from a group consisting of ethanol, glycerin, N-methyl-pyrrolidone, or dimethyl sulfoxide.

In certain aspects of the invention as described above, the co-solvent is ethanol.

In certain aspects of the invention as described above, the ethanol co-solvent has a concentration of less than about 10% w/v.

In certain aspects, the concentration of cyclophosphamide in the compositions as described above ranges from about 5 mg/mL to about 100 mg/mL.

In certain aspects, the concentration of cyclophosphamide in the compositions as described above is 10 mg/mL.

In certain aspects, the concentration of cyclophosphamide in the compositions as described above is 20 mg/mL.

In certain aspects, the cyclophosphamide compositions as described above have a pH in the range of from about 3 to about 7.5.

In one aspect, the compositions as described above are ready-to-administer (RTA) or safe-to-administer (STA).

In certain aspects of the invention, the compositions as described above exhibit prolonged room temperature stability compared to the currently approved and marketed dosage forms of cyclophosphamide.

In certain aspects of the invention, the compositions as described above exhibit prolonged room temperature stability compared to the currently manipulated dosage forms of cyclophosphamide.

In certain aspects of the invention, the compositions as described above are stable for at least 6 months when stored at 2-8° C.

In certain aspects of the invention, the compositions as described above are stable for at least 14 days when stored at 25° C./60% RH condition.

In certain aspects, the present invention relates to a stable liquid composition suitable for oral administration comprising (i) cyclophosphamide; (ii) one or more pharmaceutically acceptable solvents; and (iii) optionally, one or more pharmaceutically acceptable excipients.

In certain aspects of the invention as described above, the pharmaceutically acceptable excipient is one or more substances selected from a group consisting of stability enhancing agents, acidifying agents, surfactants, pH adjusting agents, buffering agents, solubilizers, thickening agents, anti-oxidants, anti-foaming agents, chelating agents, preservatives, flavoring agents, sweetening agents, or coloring agents.

In certain aspects of the invention as described above, the stability enhancing agent is one or more substances selected from a group consisting of oils, polyol organic solvents, or surfactants.

In certain aspects of the invention as described above, the oil is mono, -di, or triglycerides of medium-chain fatty acid ester (for example, but not limited to, Labrafac™ lipophile WL 1349, Maisine® CC, Labrasol® ALF and MIGLYOL® 812N); wherein said oil is present at a concentration from about 2.0 to about 80% by weight of composition.

In certain aspects of the invention as described above, the surfactant is a substance selected from a group consisting of at least one non-ionic surfactant, cationic surfactant, anionic surfactant, zwitterionic surfactant, or combinations thereof, wherein the surfactant is present at a concentration from about 0.1 to about 10% by weight.

In certain aspects, the compositions as described above are contained in a single-dose and/or multi-dose container. In one aspect, the composition may be contained in bottles or blow-fill seals vials. In some aspects, the bottles may be made from clear glass, amber glass, or plastic. In some aspects, the bottles may be in the range of about 0.1 mL to 100 mL in volume.

In certain aspects, the compositions as described above have RC-A impurity of less than about 0.5% (w/w) as measured by HPLC, when stored at 2-8° C. for at least 4 months.

In certain aspects, the compositions as described above are stable and retain at least 90% of the potency of cyclophosphamide when stored at a temperature from about 2-8° C. for at least 6 months.

In certain aspects, the compositions as described above are stable and retain at least 90% of the potency of cyclophosphamide when stored at 25° C./60% RH for at least 1 month.

In certain aspects, the compositions as described above have a level of total related substances that is less than about 10% (w/w) as measured by HPLC.

In certain aspects, the compositions as described above have a level of any unknown impurity that is less than about 5% (w/w) as measured by HPLC.

In certain aspects, the compositions as described above have a level of any known impurity that is less than about 5% (w/w) as measured by HPLC.

BRIEF DESCRIPTION OF THE DRAWINGS

FIG. 1 illustrates the flow chart of manufacturing procedure of composition J.

DETAILED DESCRIPTION OF THE INVENTION

Unless defined otherwise, all the technical and scientific terms used herein have the same meaning as commonly known by a person skilled in the art. In case of conflict, the definitions provided herein will prevail. Unless specified otherwise, all the percentages, portions and ratios in the present invention are on weight basis.

The term "about" when used along with a numerical variable, generally means the value of the variable and all the values of the variable within a measurement or an experimental error (e.g., 95% confidence interval for the mean) or within a specified value (e.g., ±10%) within a broader range.

As used herein, the term "cyclophosphamide" refers generically to the drug substance regardless of the crystal form, the term "cyclophosphamide monohydrate" refers specifically to the monohydrate and the term "anhydrous cyclophosphamide" refers to the anhydrous form. The monohydrate form is preferred for pharmaceutical processing, since the anhydrous form readily picks up water to form the monohydrate when exposed to a relative humidity of about 20-30% or higher at about 25° C. While the monohydrate is stable, nonetheless, under dry conditions (e.g. a relative humidity of about 20% or less), the monohydrate begins to lose this water of hydration which can reduce stability during manufacturing. Because of stability limitations which may be due in part to ready interconversion between the anhydrous and monohydrate forms, it is recommended that storage temperatures for cyclophosphamide products not exceed 30° C., and they preferably be stored at or below about 25° C. Water content of cyclophosphamide monohydrate is in between 5.7 and 6.8% w/w when measured by Karl Fischer Reagent test (KFR).

The term "pharmaceutically acceptable" substances means those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to cyclophosphamide salts which are formed with inorganic or organic acids.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

"Effective amount" or "therapeutically effective amount" mean the amount of a drug sufficient to treat, prevent, or ameliorate a condition in a subject or patient. The effective amount of cyclophosphamide or pharmaceutically acceptable salt thereof, used to practice the present invention for therapeutic management of a condition may be determined and adjusted by a person of ordinary skill to provide the appropriate amount and dosage regimen, e.g., depending upon one or more of the manners of administration, the age, body weight, sex, and/or general health of the patient.

The term "non-aqueous solvent" as used herein may be any pharmaceutically acceptable substance that would suspend and/or solubilize cyclophosphamide as described herein. Specifically, the non-aqueous solvent is a lipid solvent. More specifically, the lipid solvent is an oil.

The term "oil" as used herein may function as non-aqueous solvent or stability enhancing agent, where the function of oil particularly depends on the amount of oil used in inventive compositions as described herein. More specifically, oils may include, for example and without limitation, medium-chain fatty acid, medium-chain fatty acid esters of glycerol (e.g. mono, di or triglyceride), medium-chain fatty acid esters of polyethylene glycol, medium-chain fatty acid esters of propylene glycol, long-chain fatty acid, long-chain fatty acid esters of glycerol (e.g. mono, di or triglyceride), long-chain fatty acid esters of polyethylene glycol, long-chain fatty acid esters of propylene glycol or combinations thereof.

The term "medium-chain" is used to describe the aliphatic chain length of fatty acid containing molecules. The term "medium-chain" as used herein means any medium-chain carbon-containing substances, including $C_4$-$C_{12}$ fatty acid esters of glycerol, fatty acids, and mono-, di-, and tri-glycerides of such substances.

The term "long-chain" is used to describe the aliphatic chain length of fatty acid containing molecules. The term "long-chain" as used herein means any long-chain carbon-containing substances, including $C_{14}$-$C_{24}$ fatty acid esters of glycerol, fatty acids, and mono-, di-, and tri-glycerides of such substances.

The term "subject" refers to an animal, including a human or non-human. The terms "patient" and "subject" may be used interchangeably herein.

Within the context of this invention, the term "solution" refers to a mixture of one or more substances dispersed molecularly (i.e., dissolved) in a dissolving liquid medium or vehicle. The solution is preferably homogeneous, in the sense that API is essentially uniformly distributed and concentrated in the solution. The liquid solution may be viscous (such as syrup) or not. As already mentioned, a liquid solution differs from a suspension which comprises solid particles dispersed throughout a liquid phase in which they are not soluble.

The terms "stable" and "stability" mean the evolution of the product with time and/or under specific environmental conditions (i.e., temperature, humidity, etc.) with no significant effects on its quality, safety and/or efficacy for a given time period. It can be measured through the formation of degradation products (impurities), variation of pH, appearance (precipitation), microbial growth, and/or color. The term "stable" indicates both chemical and physical stability. The term "stable" can further mean no more than about a 10% loss of cyclophosphamide under typical commercial storage conditions. Preferably, formulations of the present inventions will have no more than about a 5% loss of cyclophosphamide, no more than about a 3% loss of cyclophosphamide, more preferably, no more than about a 2% loss of cyclophosphamide, more preferably, no more than about a 1.5% loss of cyclophosphamide under typical commercial storage conditions (i.e., 25° C./60% RH or 2-8° C.).

The term "any person" refers to any human being capable of administering a dose of cyclophosphamide composition, including physicians, healthcare professionals, nurses, pharmacists, pharmacy technicians and patients.

The term "exposure" refers to accidental contact of cyclophosphamide composition to the skin of any person while administering cyclophosphamide composition to a patient.

"Bioequivalence" refers to the absence of a significant difference between the bioavailability, i.e., the mean ratio of AUC (over 24 hours) and the mean ratio of $C_{max}$ is within 80% to 125% between two pharmaceutical drug products (e.g., a test composition and a reference composition) over the course of a period of time, at the same dose and under the same conditions. The determination of whether or not a test composition is bioequivalent to a reference composition is determined by performing a study, referred to as a bioequivalence or comparative bioavailability study, in a group of subjects under controlled conditions. The cyclophosphamide capsule product approved under NDA No. 203856 (National Drug Code Number 0054-0382) is referred to as "reference composition" in the claims, and contains cyclophosphamide as the active ingredient.

As used herein, "prolonged duration" refers to the holding a composition under controlled or uncontrolled conditions for a period of more than 14 days.

As used herein, "significant loss of potency" means no more than about 10% loss of cyclophosphamide under typical commercial storage conditions.

The present disclosure relates to stable liquid pharmaceutical compositions of cyclophosphamide, wherein cyclophosphamide is present at a concentration of 10 mg/mL or more. In one aspect, a pharmaceutical composition of the present invention comprises cyclophosphamide, wherein the concentration of cyclophosphamide ranges from about 10 mg/mL to about 600 mg/mL.

In a preferred embodiment, the stable liquid pharmaceutical composition for oral administration, comprises cyclophosphamide at a concentration of about 10 mg/mL, about 20 mg/mL, about 30 mg/mL, about 40 mg/mL, about 50 mg/mL, about 75 mg/mL, about 100 mg/mL, about 150 mg/mL, 200 mg/mL, about 250 mg/mL, about 300 mg/mL, about 350 mg/mL, about 400 mg/mL, about 450 mg/mL, about 500 mg/mL, about 550 mg/mL, about 600 mg/mL, most preferably about 100 mg/mL.

Cyclophosphamide is a nitrogen mustard derivative that is used as an anti-neoplastic agent. Cyclophosphamide occurs as a white, crystalline powder and is soluble in water and alcohol. However, as cyclophosphamide is prone to rapid hydrolytic degradation, the present invention relates to use of non-aqueous solvents for preparing pharmaceutical compositions of cyclophosphamide.

The table below illustrates saturated solubility data of cyclophosphamide in different non-aqueous solvents:

TABLE 1

| S. No. | Excipient Name | Average mg/g |
|---|---|---|
| 1 | Maisine ® CC | 132.7 |
| 2 | Miglyol ® 812 | 52.7 |
| 3 | Polyethylene glycol-400 | 133.2 |
| 4 | Propylene glycol | 336.5 |
| 5 | Labrasol ® ALF | 323.5 |
| 6 | Phosal ® 50PG | 307.7 |
| 7 | Ethanol | 247.9 |

In an embodiment, the present disclosure provides a stable solution suitable for oral administration, wherein the solution comprises (i) cyclophosphamide, (ii) at least one non-aqueous solvent, (iii) optionally one or more pharmaceutically acceptable excipients selected from a group consisting of stability enhancing agents, acidifying agents, surfactants, pH adjusting agents, buffering agents, solubilizers, thickening agents, anti-oxidants, anti-foaming agents, chelating agents, preservatives, flavoring agents, sweetening agents, coloring agents, or mixtures thereof.

In some embodiments, the present disclosure provides a stable liquid pharmaceutical composition suitable for oral administration comprising (i) cyclophosphamide, (ii) at least one non-aqueous solvent, (iii) optionally, one or more pharmaceutically acceptable excipients selected from a group consisting of acidifying agents, surfactants, co-solvent, pH adjusting agents, buffering agents, solubilizers, thickening agents, anti-oxidants, anti-foaming agents, chelating agents, preservatives, flavoring agents, sweetening agents, coloring agents, or mixtures thereof.

In some embodiments, the stability enhancing agent is a medium-chain oil comprising substantially of $C_4$-$C_{12}$ medium-chains, e.g., at least 10%, at least 20%, at least 30%, at least 40%, at least 50%, at least 60%, at least 70%, at least 80%, or at least 90% of the chains present in the oil are $C_4$-$C_{12}$. In some embodiments, the oil comprises at least one medium-chain fatty acid such as medium-chain fatty acids having at least one mono-, di-, or triglyceride, or derivatives thereof, or combinations thereof. In some embodiments, the stability enhancing agent is a long-chain oil comprising substantially of $C_{14}$-$C_{24}$ long-chains, e.g., at least 20%, at least 30%, at least 40%, at least 50%, at least 60%, at least 70%, at least 80%, or at least 90% of the chains present in the oil are $C_{14}$-$C_{24}$. In some embodiments, the oil comprises at least one long-chain fatty acid such as long-chain fatty acids having at least one mono-, di-, or triglyceride, derivatives thereof, or combinations thereof.

In an embodiment, a non-aqueous solvent as used herein is a pharmaceutically acceptable substance that would suspend and/or solubilize cyclophosphamide. More specifically, the non-aqueous solvent is an oil.

In an embodiment, the oil as used herein may function as the non-aqueous solvent or the stability enhancing agent, particularly the function of the oil depends on the amount of oil used. In a specific embodiment, oils may include, for example and without limitation, medium-chain fatty acid, medium-chain fatty acid esters of glycerol (e.g. mono, di or triglyceride), medium-chain fatty acid esters of polyethylene glycol, medium-chain fatty acid esters of propylene glycol, long-chain fatty acid, long-chain fatty acid esters of glycerol (e.g. mono, di or triglyceride), long-chain fatty acid esters of polyethylene glycol, long-chain fatty acid esters of propylene glycol or combinations thereof.

In another embodiment, the present invention provides medium-chain fatty acids selected from saturated medium-chain fatty acids, polyunsaturated medium-chain fatty acids and monounsaturated medium-chain fatty acids or mixtures thereof.

In another embodiment, the present invention provides saturated medium-chain fatty acids selected from a group consisting of hexanoic acid (also known as caproic acid), heptanoic acid (also known as enanthic acid), octanoic acid (also known as caprylic acid), nonanoic acid (also known as pelargonic acid), decanoic acid (also known as capric acid), undecanoic acid (also known as undecylic acid), or dodecanoic acid (also known as lauric acid).

In another embodiment, the present invention further comprises an unsaturated medium-chain fatty acids.

In an embodiment, the present invention provides medium-chain fatty acid esters of glycerol consisting of at least one mono-, di-, or triglyceride, derivatives thereof, or combinations thereof, wherein the medium-chain fatty acids used to form glycerides is selected from a group consisting of saturated medium-chain fatty acids, unsaturated medium-chain fatty acids or mixtures thereof.

Pharmaceutically acceptable non-aqueous solvents as described herein include, without limitation, the use of at least one of caproic fatty acid; caprylic fatty acid; capric fatty acid; tauric acid; myristic acid; succinic acid; glycerin; mono-, di-, or triglycerides and combinations and derivatives thereof; a polyethylene glycol glyceride (Labrasol® ALF and Gelucire®); a caprylic/capric triglyceride; (Miglyol® includes Miglyol® 810, 812, 816 and 829; Labrafac® lipophile WL 1349); a caproic/caprylic/capric/lauric triglyceride; a caprylic/capric/linoleic triglyceride; a caprylic/capric/succinic triglyceride; propylene glycol monocaprylate; propylene glycol monocaprate; (Capmul® PG-8 and 10; the Capmul® brands are owned by ABITEC); propylene glycol dicaprylate; propylene glycol dicaprylate; medium chain mono- and di-glycerides (Capmul® MCM); a diethylene glycol mono ester (including 2-(2-Ethoxyethoxy)ethanol: Transcutol®); diethylene glycol monoethyl ether; esters of saturated coconut and palm kernel oil and derivatives thereof; triglycerides of fractionated vegetable fatty acids, and combinations and derivatives thereof.

The preferred non-aqueous solvent is Labrasol® ALF, which self-emulsifies in the liquid media forming a fine dispersion. Labrasol® ALF consists of a small fraction of mono-, di- and triglycerides and mainly PEG-8 (MW 400) mono- and diesters of caprylic ($C_8$) and capric ($C_{10}$) acids. In a preferred embodiment, the content of Labrasol® ALF ranges from 2% to 80% by weight, more preferably 5% to 70% by weight, even more preferably 10% to 60% by weight of composition.

In another embodiment, the non-aqueous solvent is Miglyol® 812N. MIGLYOL® 812N is generally described as a $C_8$-$C_{10}$ triglyceride and it comprises at least about 80% caprylic ($C_8$) acid and capric ($C_{10}$) acid. However, it can also comprise small amounts of other fatty acids, e.g., less than about 5% of caproic ($C_6$) acid, lauric ($C_{12}$) acid, and myristic ($C_{14}$) acid. In a preferred embodiment, the content of MIGLYOL® 812N ranges from 10% to 80% by weight, more preferably 30% to 60% by weight, even more preferably 50% by weight of composition. In a preferred embodiment, the content of Miglyol® 812N ranges from 2% to 80% by weight, more preferably 5% to 70% by weight, even more preferably 10% to 60% by weight of composition.

In another embodiment, the present invention provides long-chain fatty acids selected from saturated long-chain fatty acids, polyunsaturated long-chain fatty acids and monounsaturated long-chain fatty acids or mixtures thereof.

In another embodiment, the present invention provides saturated long-chain fatty acids selected from a group consisting of myristic acid, palmitic acid, stearic acid, arachidic acid, behenic acid, lignoceric acid, cerotic acid or mixtures thereof.

In another embodiment, the present invention provides unsaturated long-chain fatty acids selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid or mixtures thereof.

In an embodiment, the present invention provides long-chain fatty acid esters of glycerol consisting of at least one mono-, di-, or triglycerides, or derivatives thereof, or combinations thereof, wherein the long-chain fatty acid used to form glycerides is selected from a group consisting of saturated long-chain fatty acids, unsaturated long-chain fatty acids or mixtures thereof.

In an embodiment, the present invention provides long-chain fatty acid esters of glycerol selected from a group consisting of at least one mono-, di-, or triglyceride, or derivatives thereof, or combinations thereof, wherein a long-chain fatty acid used to form the long-chain fatty acid esters of glycerol is selected from a group consisting of myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

In an embodiment, the present invention provides long-chain fatty acid esters of glycerol selected from the following table:

TABLE 2

| Long-chain fatty acid esters of glycerol | Commercially available products |
|---|---|
| Glyceryl mono-myristate | Nikkol ® MGM |
| Glyceryl mono-palmitate | Emalex ® GMS-P |
| Glyceryl mono-oleate | Rylo ® series, Dimodan ® series, Emuldan ® 3-4, ALDO ® MO FG, Kessco ® GMO, Monomuls ® series, Tegino ®, Drewmulse ® GMO, Atlas ® G-695, GMOrphic ® 80, ADM DMG-40, 70, and 100, Peceol ®, Hodag ® GMO-D, Myverol ® |
| Glyceryl mono-, dioleate | Capmul ® GMO-K |
| Glyceryl dioleate | Capmul ® GDO |
| Glyceryl mono-linoleate | Maisine ®; Myverol ® |
| Glycerol mono-stearate | Capmul ® GMS, Myvaplex ®, Imwitor ® 191, Cutina ® GMS, Aldo ® MS, Nikkol ® MGS series) |
| Glyceryl palmitic/stearic | Cutina ® MD-A, Estagel ®-G18 |
| Glyceryl mono-α-linolenic acid | |
| Glyceryl mono-elaidate | |
| Glyceryl mono-vaccenate | |
| Glyceryl mono-linoelaidate | |
| Glyceryl mono-arachidonate | |
| Glyceryl mono-eicosapentaenoate | |
| Glyceryl mono-erucic acid | |
| Glyceryl mono-docosahexaenoic acid | |

In another embodiment, the long-chain fatty acid ester of glycerol is a monoglyceride, wherein long-chain fatty acid used to form long-chain fatty acid esters of glycerol is linoleic acid, α-linolenic acid or mixture thereof. In another embodiment, the long-chain fatty acid ester of glycerol is Maisine® CC.

"Maisine® CC" refers to a commercial product which comprises predominantly linoleic and oleic acid mono-, di- and tri-glycerides together with minor amounts of palmitic and stearic acid mono-, di- and tri-glycerides (corn oil itself being comprised of about 56% by weight linoleic acid, 30% oleic acid, about 10% palmitic and about 3% stearic acid constituents). The physical characteristics of Maisine® are: up to 10% free glycerol; about 35% mono-glycerides; about 50% di-glycerides; about 10% triglycerides; and about 1% free oleic acid. Maisine® CC is glycerol monolinoleate that is liquid at 20° C.

In a preferred embodiment, the content of Maisine® CC ranges from 0.5 to 50% by weight, preferably 1.0 to 50% by weight, more preferably 2.0 to 40% by weight, based on the total weight of the composition.

In certain embodiments, the surfactant as used herein is selected from a group consisting of phospholipid surfactant, non-ionic surfactants, cationic surfactants, anionic surfactants, zwitterionic surfactants, or combinations thereof.

In some embodiments, the phospholipid surfactant is an amphipathic, phosphate-containing lipid, for example, a molecule containing one phosphate, a glycerol and one or more fatty acids. For example, the compositions provided herein consist of one or more phospholipid surfactant as the surfactant. Exemplary of the phospholipids used in the provided compositions are lecithin, including phosphatidylcholine (PC), lysophosphatidylcholine (LPC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof.

In another embodiment, the phospholipid surfactant (for example, but not limited to, Phosal®50PG) also functions as a lipid solvent. Phosal®50PG, comprises, by weight, not less than 50% phosphatidylcholine, not more than 6% lysophosphatidylcholine, about 35% propylene glycol, about 3% mono- and diglycerides from sunflower oil, about 2% soy fatty acids, about 2% ethanol, and about 0.2% ascorbyl palmitae. The concentration of Phosal®50PG ranges from 0.1 to 60% by weight, based on the total weight of the composition.

Non-ionic surfactants of the present disclosure generally have a hydrophobic group and a reactive hydrogen atom, for example aliphatic alcohols, acids, amides and alkyl phenols, with alkylene oxides, especially ethylene oxide either alone or in combination with propylene oxide. Examples of the non-ionic surfactant compounds include, but are not limited to, polyoxyethylene glycol sorbitan alkyl esters, block copolymers of polyethylene glycol and polypropylene glycol, ethylene glycol fatty acid esters, poly(ethylene glycol) fatty acid esters, propylene glycol fatty acid esters, poly(propylene glycol) fatty acid esters, glycol fatty acid esters, trimethylolpropane fatty acid esters, pentaerythritol fatty acid esters, glucoside derivatives, glycerin alkyl ether fatty acid esters, trimethylolpropane oxyethylene alkyl ethers, fatty acid amides, alkylolamides, alkylamine oxides, lanolin and its derivatives, castor oil derivatives, hardened castor oil derivatives, sterols and its derivatives, polyoxyethylene alkyl ethers, polyoxyethylene alkyl allyl ethers, polyoxyethylene alkylamine, polyoxyethylene fatty acid amides, polyoxyethylene alkylolamides, polyoxyethylene diethanolamine fatty acid esters, polyoxyethylene trimethylolpropane fatty acid esters, polyoxyethylene alkyl ether fatty acid esters, polyoxyethylene polyoxypropylene glycols, polyoxyethylene polyoxypropylene alkyl ethers, polyoxyethylene polyoxypropylene polyhydric alcohol ethers, glycerin fatty acid esters, polyglycerin fatty acid esters, polyoxyethylene glycerin fatty acid esters, sorbitan fatty acid esters, polyoxyethylene sorbitan fatty acid esters, sucrose fatty acid esters, or combinations thereof.

In another embodiment, the non-ionic surfactant Labrafil® M2125CS consists of mono-, di- and triglycerides and PEG-6 (MW 300) mono- and diesters of linoleic (C18:2) acid. In a preferred embodiment, the content of Labrafil® M2125CS ranges from 0.1 to 10% by weight, preferably 0.2 to 8% by weight, more preferably 0.5 to 6% by weight, based on total weight of the composition.

In some embodiments, the compositions as described herein include additional surfactants such as the zwitterionic and cationic surfactant. Examples of such surface active agents include, but are not limited to the bile acids (e.g., cholic acid, chenodeoxycholic acid, glycocholic acid, glycodeoxycholic acid, taurocholic acid, taurochenodeoxycholic acid, taurolithocholic acid, deoxycholic acid, lithocholic acid, and ursodeoxycholic acid and salts thereof, e.g., sodium, potassium, lithium), natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methyl cellulose), polyoxyethylene esters (e.g. polyoxyethylene monostearate [Myrj 45], polyoxyethylene hydrogenated castor oil (Cremophor® RH 40, Cremophor® 60), polyethoxylated castor oil (Cremophor® EL, ELP), polyoxymethylene stearate, and Solutol®), sucrose fatty acid esters, polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyllaurate, sodium lauryl sulfate, cetrimonium bromide, cetylpyridinium chloride, benzalkonium chloride, docusate sodium or combinations thereof.

In certain embodiments, the inventive compositions as described herein further comprise co-solvents. The term "co-solvent" means a non-aqueous substance, used for dissolving pharmaceutical excipients (i.e., acidifying agent, anti-oxidant, flavoring agent & sweetener) other than active ingredient. The non-aqueous co-solvent may comprise ethanol, glycerine, N-methyl-pyrrolidone, dimethyl sulfoxide, or suitable mixtures thereof. In one embodiment, the non-aqueous co-solvent is ethanol.

The amount of co-solvent that can be included in compositions of the present invention is not particularly limited. Of course, when such compositions are administered to a patient, the amount of a given co-solvent is limited to a bio-acceptable amount, which are readily determined by one skilled in the art. However, in a preferred embodiment, the concentration of co-solvent ranges from 0.01% to 15%, preferably 0.02% to 12.0%, more preferably 0.05% to 10.0%, based on total weight of the composition. In some embodiments, the concentration of co-solvent is 0%.

Further, the inventive compositions comprise one or more pharmaceutically acceptable excipients selected from a group consisting acidifying agents, pH adjusting agents, buffering agents, solubilizers, thickening agents, anti-oxidants, anti-foaming agents, chelating agents, preservatives, flavoring agents, sweetening agents, coloring agents, and mixtures thereof.

The term "sweetener" as used herein refers to both bulk (caloric) and intense (non-caloric) sweeteners, which impart sweet taste to the preparation. Examples of bulk sweeteners are dextrose, fructose, glucose, hydrogenated glucose syrup, isomalt, maltitol, maltose, mannitol, sorbitol, sucrose, xylitol, ribose, deoxyribose, neuraminic acid and mixtures thereof. Examples of intense sweeteners are acesulfame, alitame, aspartame, cyclamate, dihydrochalcone sweetener, monellin, neohesperidin, neotame, saccharin, stevioside, sucralose, the pharmaceutically acceptable salts thereof such as sodium or calcium saccharin, acesulfame potassium or sodium cyclamate, and mixtures thereof. In one embodiment, the pharmaceutically acceptable sweetener in the present invention is sucralose.

In a preferred embodiment, the concentration of sweetener ranges from 0.001% to 10%, preferably 0.005% to 8.0%, more preferably 0.007% to 7.0%, based on total weight of the composition.

The term "flavoring agent," as used herein, refers to an agent or a mixture of agents that adds flavor to a mixture. Flavoring agent is selected from a group consisting of a natural flavor, an artificial flavor, and mixtures thereof. Flavoring agents include, but are not limited to, mint, peppermint, cola, apple, vanilla, orange, peach, apricot, raspberry, cherry, honey, lemon, coconut, pineapple, strawberry banana, mixed red fruit and cream flavors and mixture thereof. In particular, the flavoring agent of the present invention is orange flavor. The concentration of flavoring agent ranges from 0.001% to 10%, preferably 0.005% to 8.0%, more preferably 0.007% to 7.0%, based on total weight of the composition.

The term "source for chloride ions" as used herein, refers to an agent or a mixture of agents that provides chloride ions as a nucleophile, by competing with other nucleophiles and hindering the degradation of the nitrogen mustard. If chloride ion attacks the aziridine ring, it tends to reform the original cyclophosphamide as opposed to resulting in the degradation of cyclophosphamide. Source of chloride ions includes by way of example and without limitation, compounds such as sodium chloride and/or potassium chloride. In an embodiment, the pharmaceutical compositions of the present invention are stable for at least 3 months, wherein the composition is free from source for chloride ions.

The pharmaceutical compositions of the present invention may additionally contain an anti-oxidant which inhibits oxidation and thus is used to prevent the deterioration of preparations by the oxidative process. Such compounds include by way of example and without limitation, sodium bisulfate, ascorbic acid, ascorbyl palmitate, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite, alpha-tocopherol and others known to those of ordinary skill in the art. In one embodiment, the pharmaceutically acceptable anti-oxidant, in the present invention is alpha-tocopherol. The concentration of anti-oxidant ranges from is 0.001% to 10%, preferably 0.005% to 8.0%, more preferably 0.007% to 7.0%, based on total weight of the composition.

The term "acidifying agent" included in the compositions described herein is capable of reducing the pH of the composition, preferably to an acidic pH. In many aspects, the acidifying agents which are suitable for inclusion in oral compositions include without limitation: organic acids such as citric, succinic, acetic, lactic and tartaric acids and inorganic acids such as phosphoric, sulphuric, hydrochloric and nitric acids. The concentration of an acidifying agent ranges from 0.001% to 30%, preferably 0.005% to 27.0%, more preferably 0.007% to 25.0%, based on total weight of the composition.

The pharmaceutical compositions of the present invention may optionally contain a preservative selected from a group consisting of benzoic acid and the sodium or potassium salts thereof, sorbic acid and the sodium or potassium salts thereof, chlorobutanol, benzyl alcohol, phenyl ethanol, methyl, ethyl, propyl or butyl-p-hydroxybenzoates, phenol, m-cresol, p-chloro-m-cresol, phenylmercury nitrate, benzalkonium chloride or mixtures thereof.

The pharmaceutical compositions of the present invention may optionally contain a buffering agent, which is used to resist change in pH upon dilution or addition of acid or alkali. Such compounds include, by way of example and without limitation, sodium dihydrogen phosphate monohydrate, disodium hydrogen phosphate anhydrous, acetic acid, sodium acetate, adipic acid, benzoic acid, sodium benzoate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium tartrate and others known to those of ordinary skill in the art.

In an embodiment, the present invention provides a stable oral liquid pharmaceutical composition comprising cyclophosphamide, wherein the composition further comprises at least one stability enhancing agent, at least one surfactant, and optionally at least one pharmaceutically acceptable excipient, wherein the solution has a pH in the range of about 1 to about 8, preferably between about 3.0 to about 7.5.

In an embodiment, the present invention provides a stable oral liquid pharmaceutical composition comprising (i) cyclophosphamide; (ii) one or more non-aqueous solvents; (iii) a stability enhancing agent selected from a group consisting of oil, polyol organic solvent; (iv) one or more surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) an oil; (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) glyceryl mono-linoleate; (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) a medium-chain oil; (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) a long-chain oil; (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) one or more polyol organic solvent; (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) polyethylene glycol (PEG); (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) propylene glycol (PG); (iv) a phospholipid surfactant; (v) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) glyceryl mono-linoleate; (iv) polyethylene glycol; (v) propylene glycol; (vi) optionally, one or more pharmaceutically acceptable excipients.

In an embodiment, the present invention provides a stable oral liquid pharmaceutical composition comprising (i) cyclophosphamide; (ii) caprylocaproyl polyoxyl-8 glyceride; (iii) a stability enhancing agent selected from a group comprising oil, polyol organic solvent; (iv) one or more surfactants; (v) optionally, one or more pharmaceutically acceptable excipients.

In another embodiment, the present invention provides a process for preparing a stable, liquid pharmaceutical formulation for oral administration, wherein the process comprises;

(a) adding cyclophosphamide to a non-aqueous solvent under stirring at room temperature to form a cyclophosphamide solution;

(b) adding one or more pharmaceutically acceptable other excipients (i.e., anti-oxidant, acidifying agent & sweetener) to at least one co-solvent under stirring at room temperature to obtain a co-solvent solution;

(c) Adding the co-solvent solution to the cyclophosphamide solution under constant stirring at room temperature to obtain a clear solution;

(d) optionally, adding at least one other pharmaceutically acceptable excipient (i.e., flavoring agent);

(e) making up the final volume with one or more non-aqueous solvents and stirring to obtain a final clear solution;

(f) filling the bulk solution into suitable container, closing with a cap, and sealing.

The pharmaceutical compositions of present disclosure may be filled into any suitable pharmaceutically acceptable containers. For example, the pharmaceutically acceptable container may be selected from a group consisting of bottles and syringes.

A bottle as used herein can be made of any material convenient for storage and use requirements such as polymers, metal and glass and so on. The bottle material does not interfere with the components of the liquid formulation as disclosed herein. In an embodiment, the bottle is made of glass. In order to protect the active ingredient from light-induced degradation, a preferred embodiment comprises a bottle made of amber glass.

In the embodiments as described above, the bottle capacity can be adapted to the volume to be administrated for the period during which the liquid formulation as disclosed herein is stable. For instance, a solution which is stable for 10 days after opening for administering two 5 mL per day doses may be stored into a bottle of about 100 mL. A person skilled in art will be able to easily adapt the volume of the bottle as needed.

The pipette as used herein is made of glass, plastic or any material convenient with the use and the storage of the liquid solutions as disclosed herein. The pipette may be graduated to facilitate the administration of the liquid solution. In an embodiment, the pipette is a 1 mL graduated pipette.

The cap (or closure) as used herein is any article for closing a suitably shaped opening. It encompasses, but is not limited to, childproof closures, waterproof closures, pipette-associated caps, solid caps, plastic or polymeric caps. In an embodiment, the cap is screwed on the bottle top or interlocked with the top of the bottle.

In the embodiments as described above, a sealing element may be required for providing tightness of the system bottle-cap or bottle-pipette-cap or bottle-pipette or pipette-cap. This element can be supplied on its own and further fit in the bottle-neck, or around the pipette, or in the cap, or it can be pre-adapted to the bottle, the cap or the pipette.

The invention also relates to a kit of parts comprising a package containing bottles of the liquid formulation as disclosed herein and pipettes intended to remove the needed amount of the liquid formulation and/or instructions.

In another aspect, the invention relates to a kit of parts allowing the extemporaneous preparation of the solutions according to the invention.

In an embodiment, the pharmaceutically acceptable container may be a bottle, wherein the bottle is selected from a group consisting of a glass bottle and a plastic bottle. Examples of glass bottle include, but are not limited to Type I, II and III borosilicate glass bottles. In an embodiment, the pharmaceutically acceptable container is a glass bottle, wherein the glass bottle may be amber color glass bottle or clear glass bottle. Examples of plastic bottles include, but are not limited to, high-density polyethylene (HDPE), and polypropylene (PP) bottles. In an embodiment, the pharmaceutically acceptable container is a plastic bottle, wherein the plastic bottle is amber, white opaque or translucent plastic bottle. In a preferred embodiment, the HDPE bottles will be available in 30, 60, 120, 250 & 500 mL fill volumes.

In an embodiment, the present disclosure provides a pharmaceutical composition packed in a kit comprising a bottle with a child resistant cap, a dosing syringe, and an adapter.

Stability: As used herein, the term "stable" is defined as no more than about 10% loss of cyclophosphamide under typical commercial storage conditions (i.e., 25° C./60% RH or 2-8° C.). In certain embodiments, the compositions of the present invention will have no more than about 5% loss of cyclophosphamide, more preferably, no more than about 4% loss of cyclophosphamide, no more than about 3% loss of cyclophosphamide, no more than about 2% loss of cyclophosphamide, no more than about 1% loss of cyclophosphamide, under typical commercial storage conditions. The composition retains at least about 90% of the potency of cyclophosphamide after storing the composition at a temperature from about 5° C. to about 25° C. for at least 1 month.

In order to understand and improve the drug's stability it is necessary to consider the degradation chemistry of cyclophosphamide. Cyclophosphamide hydrolyzes in water to four major degradation products described in USP monograph as Related Compounds A, B, C and D (RC-A, RC-B, RC-C and RC-D respectively). In aqueous media, cyclophosphamide (CP) undergoes direct hydrolysis to yield compounds RC-A and RC-C.

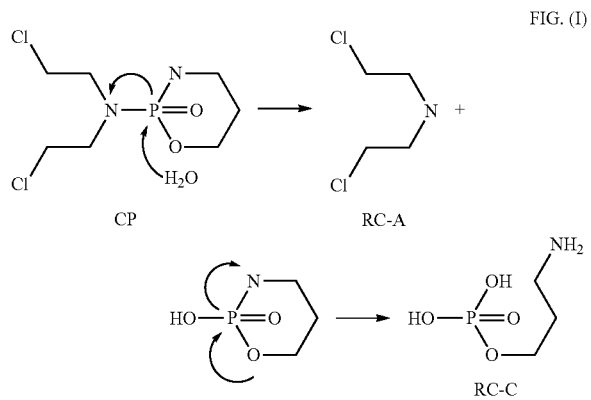

FIG. (I)

Further, intermolecular alkylation of cyclophosphamide gives an intermediate compound, which never gets detected, to further yield compound RC-B due to breakdown of P—N6 bond. Compound RC-B further yields compound RC-D due to breakdown of P—N3 bond.

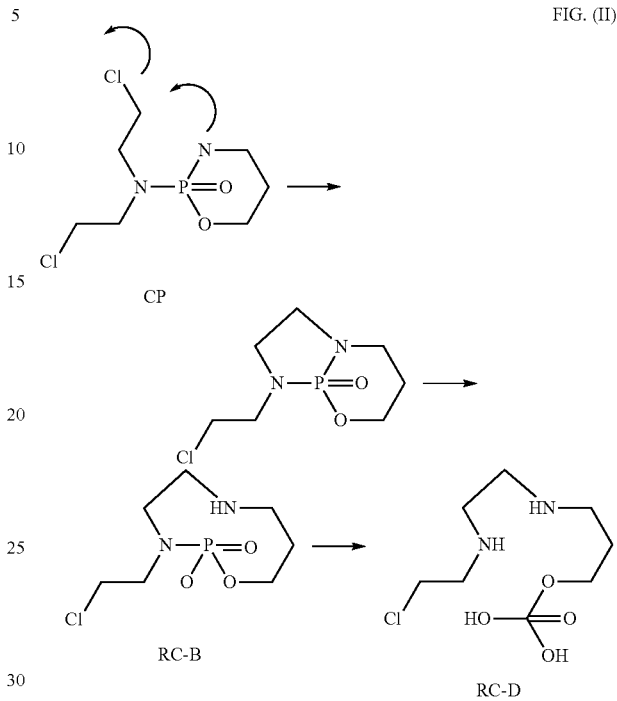

FIG. (II)

In an embodiment, the present disclosure provides stable solution of cyclophosphamide, wherein the solution comprises at least one stability enhancing agent selected from a group comprising oil, polyol organic solvent; at least one surfactant, and optionally at least one pharmaceutically acceptable excipient, wherein the level of the total impurities in the inventive solution resulting from the degradation of the cyclophosphamide in the compositions is less than about 10% as determined by HPLC after at least about 1 month at a temperature of from about 5° C. to about 25° C., and thus have long term stability for at least the same period of time or longer. Preferably, the cyclophosphamide-containing solution demonstrates long term storage stability for at least about 2 years, especially when stored at lower (refrigerated) temperatures.

In some embodiments, the pharmaceutical compositions of the present disclosure are formulated for prolonged storage of cyclophosphamide under typical commercial storage conditions (i.e., 25° C./60% RH or 2-8° C.). The pharmaceutically acceptable excipients used to formulate the composition can increase the shelf-life of cyclophosphamide when stored at room temperature. The usage of pharmaceutically acceptable excipients can decrease the rate of decomposition of cyclophosphamide at room temperature.

In an embodiment, the amount of total impurities in the inventive liquid pharmaceutical composition resulting from the degradation of the cyclophosphamide is less than about 10% (w/w), preferably less than about 5% (w/w), preferably less than about 4% (w/w), preferably less than about 3% (w/w), preferably less than about 2% (w/w), preferably less than about 1% (w/w) and more preferably less than about 0.5 (w/w) as measured by HPLC.

In another embodiment, the level of any unknown impurity in the inventive liquid pharmaceutical composition resulting from the degradation of cyclophosphamide is less than about 5% (w/w), preferably less than about 4% (w/w), preferably less than about 3% (w/w), preferably less than about 2% (w/w), preferably less than about 1% (w/w), preferably less than about 0.5% (w/w), preferably less than about 0.25% (w/w), preferably less than about 0.15% (w/w) and more preferably less than about 0.1% (w/w) as measured by HPLC.

In another embodiment, the level of compound RC-A in the inventive pharmaceutical composition resulting from the degradation of cyclophosphamide is less than about 5% (w/w), preferably less than about 4% (w/w), preferably less than about 3% (w/w), preferably less than about 2% (w/w), preferably less than about 1% (w/w), preferably less than about 0.5% (w/w), preferably less than about 0.25% (w/w), preferably less than about 0.15% (w/w) and more preferably less than about 0.1% (w/w) as measured by HPLC.

Dosage and Administration: In yet another embodiment, the invention includes methods of using stable, liquid pharmaceutical compositions of cyclophosphamide in treating malignant diseases including Hodgkin's disease, lymphocytic lymphoma, mixed-cell type lymphoma, histiocytic lymphoma, Burkitt's lymphoma, multiple myeloma, leukemias, mycosis fungoides, neuroblastoma, adenocarcinoma of ovary, retinoblastoma and breast carcinoma. The formulations of the present invention can be used to treat MCNS in pediatric patients who failed to adequately respond to or are unable to tolerate adrenocorticosteroid therapy. In an embodiment, a method of treating malignancies and MCNS in pediatric patients using stable liquid pharmaceutical compositions of cyclophosphamide, comprising orally administering to a subject from about 10 mg/mL to about 600 mg/mL of cyclophosphamide, wherein the pharmaceutical composition further comprises at least one stability enhancing agent selected from oil, polyol organic solvent and at least one surfactant and optionally at least one pharmaceutically acceptable excipient.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

In one embodiment, the dose of cyclophosphamide is in the range of from about 0.1 mg/kg/day to about 20 mg/kg/day.

In one embodiment, the dose of cyclophosphamide administered to adult or pediatric patients is 0.1 mg/kg/day, 0.2 mg/kg/day, 0.3 mg/kg/day, 0.4 mg/kg/day, 0.5 mg/kg/day, 0.6 mg/kg/day, 0.7 mg/kg/day, 0.8 mg/kg/day, 0.9 mg/kg/day, 1 mg/kg/day, 1.1 mg/kg/day, 1.2 mg/kg/day, 1.3 mg/kg/day, 1.4 mg/kg/day, 1.5 mg/kg/day, 1.6 mg/kg/day, 1.7 mg/kg/day, 1.8 mg/kg/day, 1.9 mg/kg/day, 2 mg/kg/day, 2.1 mg/kg/day, 2.2 mg/kg/day, 2.3 mg/kg/day, 2.4 mg/kg/day, 2.5 mg/kg/day, 2.6 mg/kg/day, 2.7 mg/kg/day, 2.8 mg/kg/day, 2.9 mg/kg/day, 3 mg/kg/day, 3.1 mg/kg/day, 3.2 mg/kg/day, 3.3 mg/kg/day, 3.4 mg/kg/day, 3.5 mg/kg/day, 3.6 mg/kg/day, 3.7 mg/kg/day, 3.8 mg/kg/day, 3.9 mg/kg/day, 4 mg/kg/day, 4.1 mg/kg/day, 4.2 mg/kg/day, 4.3 mg/kg/day, 4.4 mg/kg/day, 4.5 mg/kg/day, 4.6 mg/kg/day, 4.7 mg/kg/day, 4.8 mg/kg/day, 4.9 mg/kg/day, 5 mg/kg/day, 5.1 mg/kg/day, 5.2 mg/kg/day, 5.3 mg/kg/day, 5.4 mg/kg/day, 5.5 mg/kg/day, 5.6 mg/kg/day, 5.7 mg/kg/day, 5.8 mg/kg/day, 5.9 mg/kg/day, 6 mg/kg/day, 6.1 mg/kg/day, 6.2 mg/kg/day, 6.3 mg/kg/day, 6.4 mg/kg/day, 6.5 mg/kg/day, 6.6 mg/kg/day, 6.7 mg/kg/day, 6.8 mg/kg/day, 6.9 mg/kg/day, 7 mg/kg/day, 7.1 mg/kg/day, 7.2 mg/kg/day, 7.3 mg/kg/day, 7.4 mg/kg/day, 7.5 mg/kg/day, 7.6 mg/kg/day, 7.7 mg/kg/day, 7.8 mg/kg/day, 7.9 mg/kg/day, 8 mg/kg/day, 8.1 mg/kg/day, 8.2 mg/kg/day, 8.3 mg/kg/day, 8.4 mg/kg/day, 8.5 mg/kg/day, 8.6 mg/kg/day, 8.7 mg/kg/day, 8.8 mg/kg/day, 8.9 mg/kg/day, 9 mg/kg/day, 9.1 mg/kg/day, 9.2 mg/kg/day, 9.3 mg/kg/day, 9.4 mg/kg/day, 9.5 mg/kg/day, 9.6 mg/kg/day, 9.7 mg/kg/day, 9.8 mg/kg/day, 9.9 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day and 20 mg/kg/day, 25 mg/kg/day, 30 mg/kg/day, 35 mg/kg/day, 40 mg/kg/day, 45 mg/kg/day, 50 mg/kg/day. In a specific embodiment, the above-described dose of cyclophosphamide can be administered as a single dose or a divided dose over a period of 2-10 days.

In an embodiment of the invention, the dosage levels may be adjusted based on factors such as: nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

Analysis of Samples Withdrawn During Chemical Analysis of Cyclophosphamide:

The samples withdrawn were analyzed for drug content & propyl gallate using the following HPLC procedure. The materials and general conditions are listed below:

TABLE 3

| Chromatographic conditions (Drug content & propyl gallate analysis) | |
|---|---|
| Chromatographic Mode | HPLC system equipped with UV/PDA detector |
| Column | L1, 250 × 4.6 mm, 5 µm |
| Wavelength | Cyclophosphamide-195 nm & Propyl gallate-215 nm |
| Flow rate | 1.5 mL/minute |
| Injection volume | 25 µL |
| Column temperature | 25° C. |
| Temperature Sample temperature | 5° C. |
| Run time | 25 minutes |
| Mobile Phase | Mix 750 mL of 0.1% Orthophosphoric acid and 250 mL of Acetonitrile in the ratio of 75:25 (% v/v) respectively and mix well. |
| Mode of Elution | Isocratic |

The samples withdrawn were analyzed for related substances using the following HPLC procedure. The materials and general conditions are listed below:

TABLE 4

Chromatographic conditions (Related substance analysis)

| | |
|---|---|
| Chromatographic Mode | HPLC system equipped with UV/PDA detector |
| Column | L11, 4.6 × 250 mm, 3.5 µm |
| Wavelength | 200 nm |
| Flow rate | 1.0 mL/minute |
| Injection volume | 70 µL |
| Column temperature | 25° C. |
| Temperature Sample temperature | 5° C. |
| Run time | 65 minutes |
| Mobile Phase A | Buffer (pH 7.0, 20 mM phosphate buffer) solution and Methanol in the ratio of 90:10 (% v/v). |
| Mobile Phase B | Buffer (pH 7.0, 20 mM phosphate buffer) solution and acetonitrile in the ratio of 20:80 (% v/v). |

| | Gradient | |
|---|---|---|
| Mode of Elution Time | Mobile Phase-A (%) | Mobile Phase-B (%) |
| 0 | 100 | 0 |
| 5 | 100 | 0 |
| 15 | 85 | 15 |
| 25 | 70 | 30 |
| 35 | 60 | 40 |
| 45 | 50 | 50 |
| 55 | 40 | 60 |
| 55.5 | 100 | 0 |
| 65 | 100 | 0 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

TABLE 5

| Ingredients | Composition A | Composition B |
|---|---|---|
| Cyclophosphamide | 100 mg | 50 mg |
| Maisine ® CC | 0.225 mL | 0.225 mL |
| Phosal ® 50 PG | 0.025 mL | 0.025 mL |
| Alpha-tocopherol | 0.4 mg | 0.4 mg |
| Sucralose | 0.4 mg | 0.4 mg |
| Ethanol | 8.75 mg | 8.75 mg |
| Labrasol ® ALF | q.s. to 1 mL | q.s. to 1 mL |

Manufacturing Procedure of Composition A and B:

About half the quantity of Labrasol® ALF was dispensed in a manufacturing vessel. Specified amount of Maisine® CC and Phosal® 50 PG was weighed and added to the above manufacturing vessel and stirred at room temperature to obtain a clear solution. Cyclophosphamide was added to the obtained solution and stirred at room temperature. Separately alpha-tocopherol and sucralose was dissolved at room temperature in specified quantity of ethanol and stirred to obtain clear solution and this solution was added to the manufacturing vessel containing cyclophosphamide. Final volume was made up with Labrasol® ALF.

Samples of Composition A and B were stored in clear Type I glass vial for 30 days at 2-8° C. and at 25° C./60% RH conditions. Cyclophosphamide remains solubilized and compositions were found to be clear without any recrystallization or precipitation.

TABLE 6

| | Composition A Condition | | |
|---|---|---|---|
| Parameters | Initial | 2-8° C. | 25° C./60% RH |
| Duration | — | 1 month | 1 month |
| Pack | Clear Type I glass vials | Clear Type I glass vials | Clear Type I glass vials |
| Visual observation | Clear solution | Clear solution | Clear solution |
| Assay | 96.5 | 98.8 | 97.6 |

TABLE 7

| | Composition B Condition | | |
|---|---|---|---|
| Parameters | Initial | 2-8° C. | 25° C./60% RH |
| Duration | — | 1 month | 1 month |
| Pack | Clear Type I glass vials | Clear Type I glass vials | Clear Type I glass vials |
| Visual observation | Clear solution | Clear solution | Clear solution |
| Assay | 98.3 | 97.1 | 97.0 |

The Composition A and B both are physically and chemically stable for at least 1 month, without visible particles and with no significant change in assay.

Example 2

TABLE 8

| Ingredients | Composition C |
|---|---|
| Cyclophosphamide | 100 mg |
| Maisine ® CC | 0.225 mL |
| Alpha-tocopherol | 0.4 mg |
| Sucralose | 0.4 mg |
| Ethanol | 8.75 mg |
| PEG-400 | 35.0 mg |
| Propylene glycol | 35.0 mg |
| Labrasol ® ALF | q.s. to 1 mL |

Manufacturing Procedure of Composition C:

About half the quantity of Labrasol® ALF was dispensed in a manufacturing vessel. Specified amount of Maisine® CC, PEG-400 and propylene glycol was weighed and added to the above manufacturing vessel and the solution was stirred at room temperature to obtain a clear solution. Cyclophosphamide was added to the obtained solution and stirred at room temperature. Separately alpha-tocopherol and sucralose was dissolved at room temperature in specified quantity of ethanol and this solution was added to the manufacturing vessel containing cyclophosphamide. Final volume was made up with Labrasol® ALF.

Samples of Composition C was stored in clear Type I glass vial for 30 days at 2-8° C. and at 25° C./60% RH conditions. Cyclophosphamide remains solubilized and compositions were found to be clear without any recrystallization or precipitation.

TABLE 9

| Parameters | Composition C Condition | | |
|---|---|---|---|
| | Initial | 2-8° C. | 25° C./60% RH |
| Duration | — | 1 Month | 1 Month |
| Pack | Clear Type I glass vials | Clear Type I glass vials | Clear Type I glass vials |
| Visual observation | Clear solution | Clear solution | Clear solution |
| Assay | 96.8 | 100.2 | 96.9 |

The Composition C is physically and chemically stable for at least 1 month, without visible particles and with no significant change in assay.

Example 3

TABLE 10

| Ingredients | Composition D |
|---|---|
| Cyclophosphamide | 100 mg |
| Maisine ® CC | 0.225 mL |
| Phosal ® 50 PG | 0.025 mL |
| Alpha-tocopherol | 0.4 mg |
| Sucralose | 20.0 mg |
| Ethanol | 8.75 mg |
| 0.08 mg/mL Citric acid solution (pH ~4.5) | 0.016 mg |
| Labrasol ® ALF | q.s. to 1 mL |

Manufacturing Procedure of Composition D:

About half the quantity of Labrasol® ALF was dispensed in a manufacturing vessel. Specified amount of Maisine® CC and Phosal® 50 PG was weighed and added to the above manufacturing vessel and the solution was stirred at room temperature to obtain a clear solution. Cyclophosphamide was added to the obtained solution and stirred at room temperature. Separately Alpha-tocopherol and sucralose was dissolved at room temperature in specified quantity of Ethanol and this ethanolic solution was added to the manufacturing vessel containing cyclophosphamide. Thereafter, specified quantity of citric acid was added to the solution. Final volume was made up with Labrasol® ALF.

Samples of Composition D was stored in clear Type I glass vial for 30 days at 2° C.-8° C. and at 25° C./60% RH conditions. Cyclophosphamide remains solubilized and compositions were found to be clear without any recrystallization or precipitation.

TABLE 11

| Parameters | Composition D Condition | | |
|---|---|---|---|
| | Initial | 2-8° C. | 25° C./60% RH |
| Duration | — | 1 Month | 1 Month |
| Pack | Clear Type I glass vials | Clear Type I glass vials | Clear Type I glass vials |
| Visual observation | Clear solution | Clear solution | Clear solution |
| Assay | 102.3 | 102.3 | 93.1 |

The Composition D is physically and chemically stable for at least 1 month, without visible particles and with no significant change in assay.

Example 4

TABLE 12

| Ingredients | Composition E |
|---|---|
| Cyclophosphamide | 100 mg |
| Maisine ® CC | 75 mg |
| Alpha-tocopherol | 0.4 mg |
| Sucralose | 0.4 mg |
| Ethanol | 12 mg |
| DL-Tartaric acid | 0.25 mg |
| Propylene glycol | 30 mg |
| Orange (juicy) flavor (FS-335-893-2) Givaudan | 1 mg |
| Labrasol ® ALF | 100 mg |
| Miglyol ® 812N | q.s. to 1 mL |

Manufacturing Procedure of Composition E:

About half the quantity of Miglyol® 812N was dispensed in a manufacturing vessel. Specified amount of Maisine® CC, propylene glycol and Labrasol® ALF was weighed and added to the above manufacturing vessel and the solution was stirred at room temperature to obtain a clear solution. Cyclophosphamide was added to the obtained solution and stirred at room temperature. Separately alpha-tocopherol, tartaric acid and sucralose was dissolved at room temperature in specified quantity of ethanol and this solution was added to the manufacturing vessel containing cyclophosphamide. Thereafter, specified quantity of flavor was added to the solution. Final volume was made up with Miglyol® 812N.

Example 5

Cyclophosphamide compositions F, G, H, I and J are set forth in Table 13 below:

TABLE 13

| | Composition # | | | | |
|---|---|---|---|---|---|
| Ingredients | F mg/mL | G mg/mL | H mg/mL | I mg/mL | J mg/mL |
| Cyclophosphamide monohydrate | 10.7 | 10.7 | 10.7 | 10.7 | 10.7 |
| Maisine CC | — | — | 45.0 | 45.0 | 45.0 |
| Phosal ® 50 PG | 500.0 | 470.0 | 425.0 | 300.0 | 300.0 |
| Cremophor ® RH40 | — | — | — | 40.0 | 40.0 |
| Cremophor ® ELP | — | 28.0 | 28.0 | 28.0 | 28.0 |
| Ethanol | 90.0 | 90.0 | 90.0 | 90.0 | 20 |
| Tartaric Acid | 2.0 | 2.0 | 2.0 | 2.0 | 2.0 |
| Mixed berry flavor | 2.5 | 2.5 | 2.5 | 2.5 | 2.5 |
| Banana flavor | 0.75 | 0.75 | 0.75 | 0.75 | 0.75 |
| Magna Sweet 110 | 0.7 | 0.7 | 0.7 | 0.7 | 0.7 |
| Sucralose | 2.5 | 4.0 | 4.0 | 4.0 | 4.0 |
| L-Menthol | 0.35 | 0.35 | 0.35 | 0.35 | 0.35 |
| Propyl Gallate | 0.17 | 0.17 | 0.17 | 0.17 | 0.17 |
| Labrasol ® ALF | — | — | — | 85.0 | — |
| Oleic Acid | 150 | 150.0 | 150.0 | 150.0 | 250 |
| Labrafac ® Lipophile WL1349 | q.s. for 1 mL | q.s. for 1 mL | q.s. for 1 mL | q.s. for 1 mL | q.s. for 1 mL |

FIG. 1 illustrates the flow chart of manufacturing procedure of composition J.

TABLE 14

Analytical data for composition F

| | | Composition F Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 99.8 | 101.3 | 97.4 | 97.2 | 96.8 |
| Assay of Propyl Gallate | 100.4 | 105.8 | 103.2 | 100.2 | 101.1 |
| RC-A (0.618) | <BQL | ND | ND | ND | ND |
| SMUI | <BQL | ND | ND | 0.05 | ND |
| Total impurity | <BQL | ND | ND | 0.05 | ND |

Composition F was stable for at least 3 months when stored at 2-8° C. Composition F was physically and chemically stable for at least 1 month when stored at 25° C./60% RH.

Example 6

Cyclophosphamide compositions K, L, M and N are set forth in Table 15 below:

TABLE 15

| | Composition # | | | |
|---|---|---|---|---|
| | K | L | M | N |
| Ingredients | mg/mL | mg/mL | mg/mL | mg/mL |
| Cyclophosphamide monohydrate | 21.38 | 21.38 | 21.38 | 21.38 |
| Maisine ® CC | 15.0 | — | — | — |
| Phosal ® 50 PG | 45.0 | — | — | 15.0 |
| Cremophor ® RH 40 | 30 | — | — | — |
| Cremophor ® ELP | 55 | 35 | — | 35 |
| Ethanol | 90 | 90 | 90 | 90 |
| Tartaric Acid | 2 | 2 | 2.00 | 2 |
| Mixed berry flavor | 2.5 | 2.5 | 2.50 | 2.5 |
| Banana flavor | 1.5 | 1.5 | 1.50 | 1.5 |
| Sucralose | 2.5 | 2.5 | 2.50 | 2.5 |
| L-Menthol | 0.7 | 0.7 | 0.70 | 0.7 |
| Propyl Gallate | 0.35 | 0.35 | 0.35 | 0.35 |
| Labrafac ® Lipophile WL1349 | 416 | 500 | 505.00 | 500 |
| Oleic Acid | 320.0 | 350.0 | 380.00 | 335.0 |

TABLE 16

Analytical data for composition K

| | | Composition K Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 102 | 104.1 | 104.4 | 102.5 | 102.2 |
| Assay of Propyl Gallate | 100.3 | 101.9 | 101.8 | 98.0 | 100.8 |
| RC-A (0.618) | <BQL | ND | ND | ND | ND |
| SMUI | <BQL | ND | ND | ND | 0.01 |
| Total impurity | <BQL | ND | ND | ND | 0.01 |

Composition K was stable for at least 3 months when stored at 2-8° C. Composition K was stable for at least 1 month when stored at 25° C./60% RH.

TABLE 17

Analytical data for composition L

| | | Composition L Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 100.1 | 99.6 | 100.5 | 99.3 | 99.7 |
| Assay of Propyl Gallate | 101.3 | 99.7 | 100.6 | 98.4 | 96.3 |
| RC-A (0.618) | <BQL | ND | ND | ND | ND |
| SMUI | <BQL | ND | ND | ND | ND |
| Total impurity | <BQL | ND | ND | ND | ND |

Composition L was stable for at least 3 months when stored at 2-8° C. Composition L was stable for at least 1 month when stored at 25° C./60% RH.

TABLE 18

Analytical data for composition M

| | | Composition M Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 99.4 | 99.5 | 100.2 | 98.2 | 98.4 |
| Assay of Propyl Gallate | 106.0 | 104.9 | 105.7 | 104.3 | 103.6 |
| RC-A (0.618) | <BQL | ND | ND | ND | ND |
| SMUI | <BQL | ND | ND | ND | ND |
| Total impurity | <BQL | ND | ND | ND | ND |

Composition M was stable for at least 3 months when stored at 2-8° C. Composition M was stable for at least 1 month when stored at 25° C./60% RH.

TABLE 19

Analytical data for composition N

| | | Composition N Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 99.2 | 97.9 | 99.8 | 98.7 | 96.8 |
| Assay of Propyl Gallate | 103.9 | 101.7 | 104.3 | 101.3 | 99.1 |
| RC-A (0.618) | <BQL | ND | ND | ND | ND |
| SMUI | <BQL | ND | 0.06 | ND | 0.01 |
| Total impurity | <BQL | ND | 0.06 | ND | 0.01 |

Composition N was stable for at least 3 months when stored at 2-8° C. Composition N was stable for at least 1 month when stored at 25° C./60% RH.

Cyclophosphamide compositions O, P, Q, R and S are set forth in Table 20 below:

TABLE 20

| Ingredients | O mg/mL | P mg/mL | Q mg/mL | R mg/mL | S mg/mL |
|---|---|---|---|---|---|
| Cyclophosphamide | 50 | 50 | 50 | 50 | 50 |
| Maisine ® CC | 40 | — | 40 | 40 | 40 |
| Phosal ® 50 PG | 120 | — | 120 | 120 | 120 |
| Cremophor ® RH40 | — | — | — | 30 | — |
| Cremophor ® EL | 60 | 60 | 60 | 60 | — |
| Ethanol anhydrous | 90 | 90 | 90 | 90 | 90 |
| Tartaric Acid | 2 | 2 | 2 | 2 | 2 |
| Propyl gallate | 0.8 | 0.8 | 0.8 | 0.8 | 0.8 |
| Mixed berry flavor | 2.5 | 2.5 | 2.5 | 2.5 | 2.5 |
| Oleic Acid | 645 | 400 | 325 | 325 | — |
| Labrafac ® Lipophile WL1349 | — | 400 | 325 | 325 | 695 |
| Total Weight | 1010.3 | 1005.3 | 1015.3 | 1045.3 | 1000.3 |

TABLE 21

Analytical data for composition O

| | | Composition O Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 106.4 | 107.9 | 105.5 | 107.3 | 106.3 |
| Assay of Propyl Gallate | 99.7 | 101.3 | 98.7 | 100.4 | 98.5 |
| RC-A (0.618) | ND | ND | ND | 0.14 | 0.09 |
| SMUI | ND | ND | ND | 0.02 | ND |
| Total impurity | 0.00 | ND | ND | 0.19 | 0.09 |

Composition O was stable for at least 3 months when stored at 2-8° C. Composition O was stable for at least 1 month when stored at 25° C./60% RH.

TABLE 22

Analytical data for composition P

| | | Composition P Storage Condition | | |
|---|---|---|---|---|
| | | 2-8° C. | 25° C./60% RH | |
| Interval | Initial | 3 M | 1 M | 1 M |
| Pack Type | — | Glass | Glass | HDPE |
| Assay of Cyclophosphamide | 105.6 | 104.9 | 105.6 | 106.9 |
| Assay of Propyl Gallate | 100.1 | 100.1 | 100.8 | 101 |
| RC-A (0.618) | ND | ND | 0.03 | 0.01 |
| SMUI | ND | ND | 0.02 | 0.03 |
| Total impurity | ND | ND | 0.09 | 0.08 |

Composition P was stable for at least 3 months when stored at 2-8° C. Composition P was stable for at least 1 month when stored at 25° C./60% RH.

TABLE 23

Analytical data for composition Q

| | | Composition Q Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 109.2 | 109.7 | 108.0 | 110.5 | 108 |
| Assay of Propyl Gallate | 99.1 | 99.1 | 97.7 | 100.2 | 99.0 |
| RC-A (0.618) | ND | ND | ND | 0.08 | 0.07 |
| SMUI | ND | ND | ND | 0.02 | 0.03 |
| Total impurity | 0.00 | ND | ND | 0.11 | 0.10 |

Composition Q was stable for at least 3 months when stored at 2-8° C. Composition Q was stable for at least 1 month when stored at 25° C./60% RH.

TABLE 24

Analytical data for composition R

| | | Composition R Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 109.6 | 109.7 | 108.3 | 109.2 | 109.9 |
| Assay of Propyl Gallate | 100.9 | 98.5 | 98.7 | 98.7 | 98.4 |
| RC-A (0.618) | ND | ND | ND | 0.04 | 0.00 |
| SMUI | ND | ND | ND | 0.02 | 0.08 |
| Total impurity | 0.00 | ND | ND | 0.09 | 0.13 |

Composition R was stable for at least 3 months when stored at 2-8° C. Composition R was stable for at least 1 month when stored at 25° C./60% RH.

TABLE 25

Analytical data for composition S

| | | Composition S Storage Condition | | | |
|---|---|---|---|---|---|
| | | 2-8° C. | | 25° C./60% RH | |
| Interval | Initial | 3 M | 3 M | 1 M | 1 M |
| Pack Type | — | Glass | HDPE | Glass | HDPE |
| Assay of Cyclophosphamide | 107.9 | 106.6 | 106.1 | 110.5 | 108.0 |
| Assay of Propyl Gallate | 100.1 | 99.4 | 99.7 | 100.2 | 99.0 |
| RC-A (0.618) | ND | ND | ND | 0.03 | ND |
| SMUI | ND | ND | ND | 0.09 | 0.09 |
| Total impurity | 0.00 | ND | ND | 0.25 | 0.24 |

Composition S was stable for at least 3 months when stored at 2-8° C. Composition S was stable for at least 1 month when stored at 25° C./60% RH.

Example 7

Cyclophosphamide compositions T, U, V, W, X and Y are set forth in Table 26 below:

TABLE 26

| Ingredients | T mg/mL | U mg/mL | V mg/mL | W mg/mL | X mg/mL | Y mg/mL |
|---|---|---|---|---|---|---|
| Cyclophosphamide monohydrate | 100 | 100 | 100 | 100 | 100 | 100 |
| Maisine ® CC | — | 75 | 75 | 75 | 75 | 75 |
| Phosal ® 50 PG | 100 | 200 | — | — | 50 | — |
| Alpha-Tocopherol | 0.4 | — | — | — | — | — |
| Ethanol anhydrous | 75 | 125 | 125 | 90 | 90 | 90 |
| Tartaric Acid | — | — | — | 0.25 | 2 | — |
| Cysteine HCl•H$_2$O | 0.5 | 1 | 0.5 | — | — | — |
| Citric acid anhydrous | — | — | — | — | — | 2 |
| Propyl gallate | — | 1.5 | 1.5 | 1.5 | 1.5 | 1.5 |
| Mixed berry flavor | 2.5 | 2.5 | 2.5 | 2.5 | 2.5 | 2.5 |
| Labrafac ® Lipophile WL1349 | q.s. to 1 mL | q.s. to 1 mL | q.s. to 1 mL | q.s. to 1 mL | q.s. to 1 mL | q.s. to 1 mL |

TABLE 27

Analytical data for composition V and X

| | Composition V | | | Composition X | | |
|---|---|---|---|---|---|---|
| Storage condition | 2-8° C. | 2-8° C. | 25° C./60% RH | | 2-8° C. | 25° C./60% RH |
| Duration | Initial | 4 M 20 days | 1 M | Initial | 3 M 23 Days | 3 M 23 Days |
| Assay (%) of cyclophosphamide | 94.0 | 94.6 | 99.0 | 100.1 | 100.6 | 98.7 |
| Assay (%) of propyl gallate | NP | 82.4 | 99.3 | NP | 94.2 | 92.8 |

Composition V was stable for at least 4 months when stored at 2-8° C. Composition V was stable for at least 1 month when stored at 25° C./60% RH.

Composition X was stable for at least 3 months when stored at 2-8° C. Composition X was also stable for at least 3 months when stored at 25° C./60% RH.

TABLE 28

Analytical data for composition Y

| | Composition Y | | |
|---|---|---|---|
| Storage condition | | 2-8° C. | 25° C./60% RH |
| Duration | Initial | 3 M 23 Days | 3 M 23 Days |
| Assay (%) of cyclophosphamide | 101.2 | 93.9 | 105.0 |
| Assay (%) of propyl gallate | NP | 92.4 | 92.9 |

Composition Y was stable for at least 3 months when stored at 2-8° C. or at 25° C./60% RH.

While the invention has been described above with reference to specific embodiments thereof, it is apparent that many changes, modifications, and variations can be made without departing from the inventive concept disclosed herein, and such description is not intended as limitations on the scope thereof. Accordingly, it is intended to embrace all such changes, modifications, and variations that fall within the spirit and broad scope of the appended claims.

We claim:

1. A stable, ready-to-administer, liquid composition for oral administration comprising:
   (i) cyclophosphamide at a concentration of about 10 mg/ml;
   (ii) a non-aqueous lipid solvent is selected from a group consisting of phospholipids, medium-chain fatty acids, medium-chain fatty acid esters of glycerol, medium-chain fatty acid esters of polyethylene glycol, medium-chain fatty acid esters of propylene glycol, long-chain fatty acids, long-chain fatty acid esters of glycerol, long-chain fatty acid esters of polyethylene glycol, long-chain fatty acid esters of propylene glycol, or combinations thereof; and
   (iii) a co-solvent selected from ethanol and glycerin;
   wherein a concentration of the non-aqueous lipid solvent ranges from about 60% to 99% by weight of the composition;
   wherein a concentration of the co-solvent is less than 10% by weight of the composition; and
   wherein a level of total impurities in said liquid composition is less than 5% as determined by HPLC when stored at 2-8° C. for at least 3 months.

2. The composition of claim 1, wherein the composition has a RC-A impurity of less than about 1% (w/w) as measured by HPLC, when stored at 2-8° C. for at least 3 months.

3. The composition of claim 1, wherein the composition has a pH in the range of from about 3 to about 7.5.

4. The composition of claim 1, wherein the liquid composition is a solution.

* * * * *

UNITED STATES PATENT AND TRADEMARK OFFICE
CERTIFICATE OF CORRECTION

PATENT NO. : 11,931,370 B2
APPLICATION NO. : 17/961943
DATED : March 19, 2024
INVENTOR(S) : Shailendra Mandge et al.

It is certified that error appears in the above-identified patent and that said Letters Patent is hereby corrected as shown below:

On the Title Page

Please insert item (30) as follows:
--(30) Foreign Application Priority Data
Oct. 8, 2021 (IN) ................................ 202141046000--

Signed and Sealed this
Fourteenth Day of May, 2024

Katherine Kelly Vidal
*Director of the United States Patent and Trademark Office*